| United States Patent [19] | [11] | 4,354,041 |
|---|---|---|
| Bellis | [45] | Oct. 12, 1982 |

[54] METHOD FOR DEACTIVATING CATALYST IN PREPARATION OF DIMETHYLFORMAMIDE FROM DIMETHYLAMINE AND CARBON MONOXIDE

[75] Inventor: Harold E. Bellis, Wilmington, Del.

[73] Assignee: E. I. Du Pont de Nemours and Company, Wilmington, Del.

[21] Appl. No.: 193,834

[22] Filed: Oct. 3, 1980

[51] Int. Cl.³ .................................... C07C 102/00
[52] U.S. Cl. .................................... 564/123
[58] Field of Search .................................... 564/132

[56] References Cited

U.S. PATENT DOCUMENTS 2,866,822  12/1958  Siefen et al. .................... 564/132

FOREIGN PATENT DOCUMENTS 1142163  1/1963  Fed. Rep. of Germany ...... 564/132
1146869  4/1963  Fed. Rep. of Germany ...... 564/132
1215130  4/1966  Fed. Rep. of Germany ...... 564/132

*Primary Examiner*—Charles F. Warren

[57] ABSTRACT

The alkali metal methylate catalyst used in the catalytic preparation of dimethylformamide from dimethylamine and carbon monoxide is deactivated by bringing it into contact with an alkyl formate.

4 Claims, No Drawings

METHOD FOR DEACTIVATING CATALYST IN PREPARATION OF DIMETHYLFORMAMIDE FROM DIMETHYLAMINE AND CARBON MONOXIDE

DESCRIPTION

Technical Field

This invention relates to a method for deactivating the alkali metal methylate catalyst used in the catalytic preparation of dimethylformamide (DMF) from dimethylamine (DMA) and carbon monoxide. It is more particularly directed to such a method in which the catalyst is deactivated by bringing it into contact with an alkyl formate.

BACKGROUND AND SUMMARY OF THE INVENTION

DMF is a commodity in the chemical industry, widely used as a solvent and as a reaction medium in the preparation of dyes.

One method for preparing DMF on a commercial scale is that in which dimethylamine and carbon monoxide are catalytically reacted, using an alkali metal methylate as the catalyst. This produces crude DMF, which must be refined to be commercially acceptable. Before this is done, it is customary to deactivate the catalyst before the crude DMF is fed to the refining train because its presence in the train causes decomposition of DMF product into DMA and formic acid, for obvious reasons an undesirable thing.

This deactivation is ordinarily done by adding water to the reaction mass just before it is fed to the refining train. This deactivates the catalyst, as shown by the following illustrative equation:

$$XOCH_3 + H_2O \longrightarrow CH_3OH + XOH \quad (1)$$

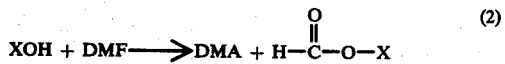

where

X is an alkali metal.

The alkali metal formate (I) which forms is insoluble in the reaction mass, precipitates and can be removed by filtration or centrifugation.

However, as can be seen from equation (2), this method of deactivating the catalyst exacts an economic penalty since some of the product DMF is consumed. This yield loss can amount to as much as 2%, by weight.

It has now been found that the alkali metal methylate catalyst can be deactivated without this disadvantage by bringing the reaction mass into contact with an alkyl formate at the end of the reaction. The alkyl formate can be added directly, or it can be generated in the reaction mass in situ.

DETAILED DESCRIPTION OF THE INVENTION

"Alkyl formate" as used herein, means a formate whose alkyl radical contains 1–3 carbon atoms, i.e., methyl-, ethyl- or propyl formate.

The formate deactivates the catalyst as shown in the following equation:

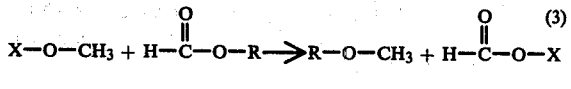

where

X is an alkali metal, and

R is an alkyl radical of 1–3 carbon atoms.

The alkali metal formate precipitate (I) is removed from the product as before, and the ether which is produced passes from the reactor as an off-gas or dissolves in the product and is removed by subsequent refining.

The DMA-carbon monoxide reaction is run by first charging a suitable reaction vessel with DMF. To this is added 0.25–1%, by weight of the DMF, of alkali metal methylate catalyst, preferably sodium methylate. The catalyst is added as a 0.5–5% solution in methanol.

To this catalyst-DMF mixture is then added 10–25%, by weight of the mixture, of DMA. The resulting reaction mass is then continuously stirred and its temperature is brought to and held at 20°–160° C., preferably 60°–130° C. The reactor is then pressurized to 275–930 kPa (40–135 psi), preferably 620–860 kPa (90–125 psi) with carbon monoxide.

After the DMA has been consumed, as determined by periodic sampling and analysis by titrating with acid, the alkyl formate, preferably methyl formate, is added to the reaction mass in an amount equimolar to that of the catalyst. The DMF product is then withdrawn from the reactor and refined by conventional methods.

In a preferred alternative, the alkyl formate can be generated in situ at the end of the DMA-carbon monoxide reaction by maintaining the carbon monoxide pressure in the reactor for 15–30 minutes after the DMA-carbon monoxide reaction is finished.

Alkyl formate is formed, as shown by the illustrative equation:

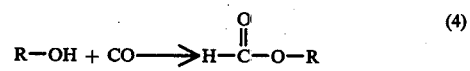

where

R is an alkyl radical of 1–3 carbon atoms.

The alkyl formate then deactivates the catalyst, as previously shown in equation (3).

The DMA-carbon monoxide reaction can also be run continuously, as shown in U.S. Pat. No. 2,866,822, which is incorporated into this specification to show the details of the process.

Briefly, according to that process, DMA and a solution of methylate catalyst in an alkanol are introduced into a vertical reaction column at its top. The DMA and catalyst solution flow downwardly through the column, which has been prefilled with DMA. Carbon monoxide is introduced at the bottom of the column and flows upwardly, or countercurrent to the flow of DMA and catalyst solution. Product DMF is removed from the bottom of the column.

The alkyl formate can be introduced into the reaction column at an appropriate point, preferably near the bottom, so that the catalyst is deactivated in a zone immediately adjacent to the reactor outlet. The actual amount of alkyl formate added is important only in the sense that enough is added to completely deactivate all the catalyst in the product to be withdrawn. To make sure of this, enough alkyl formate can be added so that about 1%, by weight, of it appears in the reactor effluent, as measured by conventional continuous gas chromatographic methods.

An alternative to the method just described is one in which the alkyl formate is formed in the reaction mass in situ. This is done by using an excess over the stoichiometric amount of carbon monoxide, and by introducing the alkali metal methylate catalyst into the reaction mass as a solution in an alkanol of 1-3 carbon atoms, preferably methanol. The amount of carbon monoxide fed into the reactor, and its ratio to the amount of DMA fed in, is such that at least about 1%, by weight, of alkyl formate will appear in the reactor effluent. This, as before, is measured by continuous gas chromatography. When the level of alkyl formate in the reactor effluent falls below about 1%, it can be brought back to the proper level by simply increasing the flow of carbon monoxide to the reactor, or by decreasing the flow of DMA.

For the process of the invention to function at maximum efficiency, it is highly desirable that the reaction mass contain no more than about 0.02-0.03%, by weight, of water.

After the alkali metal formate precipitate has been removed from the reactor effluent, the product DMF can be fed directly to a conventional refining train, usually a distillation column, with no further processing or treatment.

BEST MODE

In the following description, all parts are by weight.

A reactor was charged with 140 parts of DMF and to this were added (a) a solution of 0.9 part of sodium methylate in 39 parts of methanol and (b) 21 parts of DMA. The reactor was pressurized with carbon monoxide (690 kPa, 100 psi) and brought to and held at a temperature of 90° C. for 30 minutes, with continuous stirring to allow complete reaction of the DMA. The reaction mass was then held at that temperature and pressure for an additional 45 minutes to allow formation of methyl formate and its subsequent reaction with the sodium methylate catalyst.

At the end of that period, the pressure was released and the reactor opened. The alkali metal formate and ether byproduct were removed by filtration and distillation, and the resulting DMF was then ready for refining.

I claim:

1. In the process of catalytically preparing dimethylformamide by the reaction of dimethylamine and carbon monoxide in which an alkali metal methylate is used as the catalyst, a method for deactivating the catalyst at the end of the reaction, the method comprising bringing the catalyst into contact with enough of an alkyl formate whose alkyl group contains 1-3 carbon atoms to deactivate the catalyst.

2. The method of claim 1 in which the alkyl formate is generated in situ by introducing the catalyst into the reaction mass as a solution in an alkanol of 1-3 carbon atoms and conducting the dimethylamine-carbon monoxide reaction under conditions such that an excess over the stoichiometric amount of carbon monoxide is present.

3. The method of claim 1 in which the catalyst is sodium methylate and the alkyl formate is methyl formate.

4. The method of claim 2 in which the alkyl formate is methyl formate.

* * * * *